United States Patent [19]

Linklater et al.

[11] Patent Number: 4,521,433

[45] Date of Patent: Jun. 4, 1985

[54] PROCESS FOR CHEESE MAKING

[75] Inventors: Peter M. Linklater, Randwick; George W. Browning, Coogee, both of Australia

[73] Assignee: The Commonwealth of Australia, Belconnen, Australia

[21] Appl. No.: 540,994

[22] Filed: Oct. 11, 1983

[30] Foreign Application Priority Data

Oct. 13, 1982 [AU] Australia ............... PF6328

[51] Int. Cl.³ .............................. A23C 19/00
[52] U.S. Cl. ...................... 426/36; 436/22; 436/163; 436/177
[58] Field of Search ............ 426/36, 40, 41, 61, 426/231, 582; 436/163, 22, 23, 177

[56] References Cited

U.S. PATENT DOCUMENTS

| | | |
|---|---|---|
| 1,616,092 | 2/1927 | Stirlen . |
| 1,659,529 | 2/1928 | Hyuga . |
| 2,141,698 | 12/1938 | Saunders ............... 99/116 |
| 2,216,976 | 10/1940 | Langelier ............... 88/14 |
| 2,247,008 | 6/1941 | Assmus ................. 88/14 |
| 4,218,534 | 8/1980 | La Belle et al. ....... 426/41 |
| 4,372,979 | 2/1983 | Reinbold et al. ....... 426/41 |
| 4,415,594 | 11/1983 | Czulak et al. .......... 426/36 |

OTHER PUBLICATIONS

Donald D. Van Slyke et al., Photometric Determination of pH with a Single Standard and Calculation by Nomogram, Clinical Chemistry, vol. 12, No. 12, 1966, pp. 849–870.

J. Sendroy, Jr. et al., Indicator Activity Coefficients—C-1928, pp. 212–245.

T. B. Smith, et al., The Use of the Spekker Photoelectric Absorptiometer for the Determination of pH, Journal of the Chemical Society, 1952, pp. 3848–3854.

Donald D. Van Slyke et al., Photometric Measurement of Plasma pH, 1948 or 1949, pp. 743–756.

Primary Examiner—Raymond Jones
Assistant Examiner—Marianne S. Minnick
Attorney, Agent, or Firm—Owen, Wickersham & Erickson

[57] ABSTRACT

The acidity of whey is measured to an accuracy of 0.01 pH units by the steps of: clarification to remove fines, dilution with a solution of indicator, and spectrophotometric determination of the absorbances at one or two wavelengths characteristic of the indicator.

3 Claims, 1 Drawing Figure

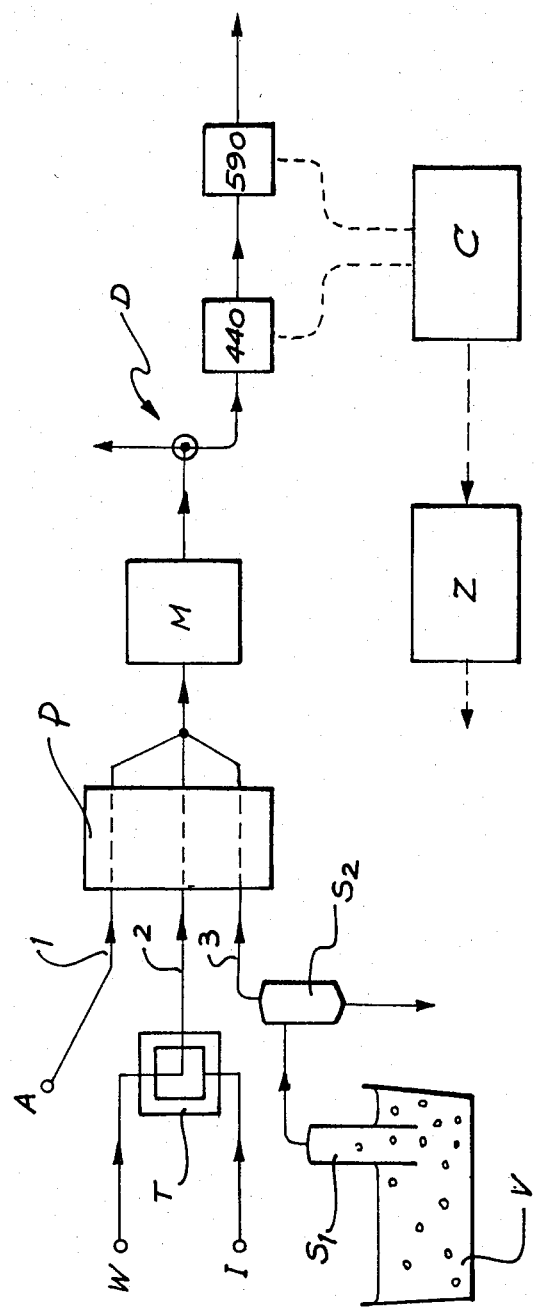

PROCESS FOR CHEESE MAKING

The present invention relates to a process of making cheese, and in particular to a process of determining the pH of the whey which is suitable for improving the control of the cheese making process.

In outline, cheese is made as follows. Firstly, starter (i.e. a culture of suitable bacteria) and rennet are added to the milk, which is then left to coagulate. Then, the coagulated milk is cut into small cubes, and generally stirred and cooked to expel whey, which is also promoted by the production of lactic acid. At the correct pH, the liquid whey is then separated off from the semi-solid curd. The curd is then processed further to the finished cheese by packing, cheddaring, milling, addition of salt and finally pressing. Although many factors go to make a successful cheese, it is well known that one of the most critical factors is the treatment of the curd between cutting and separation of the whey. It is very important that the pH of the whey be at a correct level when the curd is separated off.

However, accurate monitoring of the pH of the whey poses significant problems. Typically, between cutting and separation of the curd, the pH of the whey may fall by only a relatively small amount e.g. from around 6.5 to around 6.2. Furthermore, it may be necessary to determine very accurately the pH at which the whey is drawn off. Generally, whey comprises a complex turbid mixture of water, curd fines, fat globules, proteins and solutes. The accurate determination of its pH is thus problematical. Conventional pH meters using glass electrodes have been found unsatisfactory for routine use since the various whey constituents gradually foul the glass electrode.

Indicators, usually in the form of pH paper, are often used to estimate the pH of solutions or hydrated solids. Roeder (Dairy Sci.Abs.12,315 (1950)) visually estimated the pH of whole milk by the addition of bromothymol blue, comparing the colour to a reference chart, to an accuracy of about 0.05 pH units. However, this method does not seem to be entirely accurate and Talce (Dairy Sci.Abs.12,316 (1950)) using Roeder's method found a standard deviation of about 0.2 pH units. Such visual estimation techniques are inherently unreliable since they require visual comparison of a coloured turbid solution with a standard colour chart.

Alternatively, the prior art has measured the acidity of whey solutions by titrating the whey to an end point detected by an indicator. However, such methods may also be unreliable, due to difficulties in accurately establishing the end point of the titration, and also to uncertainties inherent in the subtraction of two relatively large titres to obtain the desired pH change.

Thus, up to the present there has been no reliable method of monitoring the changes in pH of the whey to the required accuracy (preferably to 0.01 pH units). The present inventors have discovered that it is surprisingly possible to obtain accurate measurements of the whey pH by spectrophotometrically determining the absorption of whey to which a suitable indicator has been added.

Spectrophotometric determination of pH is not new, and has for example been used to determine the pH of blood plasma. Such techniques were developed during the early part of this century before the availability of reliable glass electrodes. However, there is no suggestion in the literature that this method of measuring pH might prove successful when applied to the measurement of the pH of the highly heterogeneous turbid whey formed in the cheese making process.

In summary, the present invention provides a process of making cheese which comprises the steps of:
(a) coagulating milk,
(b) cutting the coagulum to produce curd and whey,
(c) withdrawing a sample of whey,
(d) clarifying the whey to remove fines,
(e) mixing an indicator with the sample, the indicator having an absorbance at a wavelength in the visible region characteristic of a coloured form of the indicator,
(f) determining the optical absorption of the mixture, and deriving the pH of the whey from the absorption,
(g) separating the curd and whey at a chosen pH, and
(h) further processing the separated curd into cheese.

The step of coagulating the milk is carried out according to well known practice, for example by adding starter and rennet.

After the coagulum has been cut, the mixture of curd and whey will be processed according to desired practice so that when the curd is separated from the whey it has the desired characteristics of moisture content and acidity. Generally, the curd and whey mixture is stirred and then cooked at a temperature of around 38° to 40° C. The processing of the curd in the whey is very important in determining the properties of the finished cheese. During this time (usually in the range 120-150 mins), it is desirable to monitor the pH to an accuracy of at least 0.01 pH units.

The sample of whey which has been withdrawn generally contains fines, which are separated off before the sample is mixed with the indicator. A number of clarifying techniques such as filtration and centrifugation may be used. However, it is preferred to employ a settling tube from which clarified whey is withdrawn at an upper end thereof.

In one embodiment of the invention, the absorption of the mixture is determined at a single wavelength. Knowing the exact concentration of the indicator it is then possible to calculate the whey pH. Alternatively, a dye which is unaffected by changes in pH could be added to the indicator to act as a standard and its concentration measured by absorption at a different wavelength. Preferably, a differential colorimeter is employed, wherein a mixture of whey with an aqueous indicator solution is passed through one cell and a mixture of whey and water is passed through the other cell to provide a blank comparison. A suitable indicator has been found to be 4-nitrophenol which has a $pK_a$ of about 7.1. This indicator shows a low tendency to bind to protein in the whey.

In this embodiment, for maximum sensitivity the indicator is preferably chosen such that if the coloured form is in the alkaline region, the $pK_a$ is greater than the pH of the whey; and vice-versa if the indicator is coloured in the acid region.

In another embodiment, an indicator having two absorbances in the visible region is used and the ratio of the absorptions of the mixture at the two wavelengths is determined.

The indicator should have a $pK_a$ value which lies in the pH region of interest. This ensures that each of the two absorbances has a measurable value over the pH range. Generally, the indicator will have a $pK_a$ value in the region 5.5 to 7.0. Preferred indicators include bromocresol purple, methyl red, and chlorophenol red.

Bromocresol purple is the preferred indicator and has a $pK_a$ value of 6.3. The non-ionised form of the indicator absorbs at 433 nm and the ionised form absorbs at 591 nm.

Preferably, the mixture including the indicator is passed sequentially through two cells of a spectrophotometric comparator. The pH is determined from the ratio as follows.

The dissociation constant $K_a$ is related to the concentration of hydrogen ions $H^+$, the concentration of ionised indicator $I^-$ and non-ionised form HI by the equation (1)

$$K_a = \frac{[H^+][I^-]}{[HI]} \quad (1)$$

pH is determined from equations (2) and (3)

$$pH = pK_a - \log \frac{[HI]}{[I^-]} \quad (2)$$

$$pH = pK_a - \log \left( \frac{C.Abs(433)}{D.Abs(591)} - E \right) \quad (3)$$

where C, D and E are constants. The value of E is the ratio of the absorbance at 433 nm to that at 591 nm for the indicator totally in the ionised $I^-$ form.

Binding of the indicator to proteins in the whey has proved to be a problem in some circumstances and can lead to errors in the pH measured. It is thus desirable to choose an indicator which shows minimum binding to the proteins. It is also possible to add a substance which competes successfully with the indicator in binding to the proteins, for example 2-naphthalene sulphonate.

Experiments have shown that possible errors arising from binding of calcium ions present in the whey to the indicator are generally negligible.

In this way, the pH of the whey may be continuously monitored during the processing of the curd and whey mixture. When the whey has reached the desired pH, the whey is then drawn off according to known techniques. However, it is desirable in an industrial cheese making process that the processing of the curd and whey be accomplished within a constant time interval. Under such circumstances, the monitoring of the pH may be used to give information regarding control of the processing conditions such that the desired pH is attained at the end of the given time interval. For example, monitoring of the pH may be used to control the amount of starter added to a subsequent batch of milk. Alternatively, the temperature of a subsequent batch may be modified so as to speed up or slow down the process.

The process may be further controlled by conducting separate trials relating to the growth rate of bacteria in the starter used to coagulate the milk, so as to ascertain the activity of the starter before it is added to a batch of milk. It may also be desirable to conduct small scale coagulation trials so as to establish the general processing conditions required for each batch. In this way variations in parameters such as milk type and quality and starter activity can be allowed for.

After the curd has been separated from the whey, the curd is further processed according to known techniques to produce the finished cheese.

The invention also provides an apparatus for use in the process.

Embodiments of the present invention will now be described by way of example only, with reference to the accompanying drawing, which is a block diagram of a whey sampling system.

In the drawing, the mixture of curd and whey is contained in vat V. Whey is sucked out of the vat through settler $S_1$ in which the rate of withdrawal of whey is much less than the rate of settling of the curd fines suspended in the whey. The clarified whey then passes to a further settler $S_2$ and the further-clarified whey is withdrawn from the top, whilst the remaining whey is removed from the bottom outlet.

The whey is pumped by peristaltic pump P to mixing chamber M. Alternatively, a mixing coil might be used. The pump has three lines 1, 2 and 3. Air A is drawn through line 1, whilst either water W or indicator 1 is drawn through line 2. The air, water or indicator, and clarified whey are then mixed together in the mixing chamber. The air bubbles serve to ensure complete mixing of the indicator and whey. The use of a peristaltic pump ensures that metered quantities of indicator are added to metered amounts of clarified whey.

In the debubbler D, the air is separated from the mixture of whey and indicator and leaves through the top of the debubbler. The mixture of whey and indicator then passes through two cells of spectrophotometric comparator C, the first cell measuring the absorption of the mixture at approximately 440 nm and the second cell measuring the absorption at approximately 590 nm. 1 mm light path flow cells are used to reduce the attenuating affect of whey turbidity. The comparator establishes the ratio of the absorptions of the ionised and non-ionised forms. This ratio is then passed to control unit Z which comprises a computer which calculates the pH value and uses this value to control the processing conditions (for example, the amount of starter added to a subsequent batch).

For the indicator bromocresol purple, the relationship between the pH and the ratio of absorptions was found to be determined by equation (4)

$$pH = 5.861 - 1.167 \log \left( \frac{Abs(433)}{Abs(591)} - 0.02 \right) \quad (4)$$

The constant 1.167 (rather than the theoretical value of unity) is believed to be the result of binding of the indicator to whey protein.

In order to allow for the turbidity of the whey in the absence of indicator at the two different wavelengths, a three-way tap T is included to enable water or indicator to be switched on at repeated intervals, thereby establishing the optical density of the whey in the absence of indicator. It was found that, provided the zero light setting is known, variations in turbidity of the whey do not cause significant error.

Errors caused by variations in the ionic strength of the whey have been found to be negligible.

As mentioned earlier, errors caused by binding of the protein in the whey to the indicator may be significant under certain circumstances and for this reason, the technique is best suited to measuring changes in pH rather than absolute pH levels.

The apparent pH has also been found to vary slightly with temperature, so that it is preferable that the spectrophotometric measurements be conducted at constant temperature.

It has been surprisingly discovered that using this method the pH of the whey may be established to an accuracy of 0.01 pH units, despite the turbidity and inhomogeneity of the whey. Even under ideal conditions, such accuracy is not attainable with a pH meter, whose performance in any case degrades rapidly due to fouling by the whey and is thus unsuitable for regular use.

A second embodiment of the invention employs a differential colorimeter to measure absorption at a single wavelength. A suitable indicator has been found to be 4-nitrophenol which is yellow in the alkaline form and colourless in the acid form, and absorbs at 420 nm.

A mixture of indicator solution and whey is passed through one cell of the differential colorimeter, whilst a mixture of water and whey is passed through the other cell to act as a standard. The mixtures are supplied to the differential colorimeter using a peristaltic pump and a pair of flow lines analogous to the flow line shown in the drawing.

The pH is calculated from a knowledge of the concentration of indicator according to known relationships.

We claim:

1. A process of making cheese having a desired pH which comprises the steps of
(a) coagulating milk,
(b) cutting the coagulum to produce curd and whey,
(c) continuously monitoring the pH of the whey by withdrawing a sample of whey from said curd and whey,
(d) continuously treating the sample of whey to remove fines by
    (i) passing the whey upwardly up a settling tube such that the rate at which the whey passes upwards is less than the rate of settling of the fines, and
    (ii) filtering the treated sample of whey to further remove fines, resulting in a turbid whey sample;
(e) mixing an indicator with said treated filtered whey sample, the indicator
    (i) having an absorbance at the wavelength in the visible region characteristic of a coloured form of the indicator,
    (ii) having substantially no tendency to bind to milk proteins in said whey sample, and
    (iii) having a $pK_a$ value in the region 5.5 to 7.1;
(f) determining the optical absorption of said indicator-whey mixture, and deriving the pH of the whey sample from said absorption;
(g) separating the curd and whey at a desired pH; and
(h) further processing the separated curd into cheese having the desired pH.

2. A process according to claim 1 wherein the indicator has absorbances at two wavelengths in the visible region, which comprises determining the absorption of the mixture at each of the two wavelengths, and deriving the pH of the whey from the ratio of the two absorptions.

3. A process according to claim 1 wherein the indicator is bromocresol purple.

* * * * *